US00PP08900P

United States Patent [19]

Dickson

[11] Patent Number: Plant 8,900

[45] Date of Patent: Sep. 20, 1994

[54] FLORIBUNDA ROSE PLANT NAMED DICQUIET

[75] Inventor: Patrick Dickson, Newtownards, Northern Ireland

[73] Assignee: Bear Creek Gardens, Inc., Medford, Oreg.

[21] Appl. No.: 138,761

[22] Filed: Oct. 18, 1993

[51] Int. Cl.[5] ..... A01H 5/00

[52] U.S. Cl. ..... Plt./22

[58] Field of Search ..... Plt. 22, 24

*Primary Examiner*—Howard J. Locker

*Attorney, Agent, or Firm*—Klarquist Sparkman Campbell Leigh & Whinston

[57] ABSTRACT

Rose plant of floribunda class having distinctive yellow and orange colored flowers; dark green, healthy, disease-resistant foliage; and upright, well-branched growth habit.

1 Drawing Sheet

The present invention relates to a new and distinct variety of rose plant of the floribunda class which was originated by me by crossing the variety DICmagic with the variety MACmanly, U.S. Plant Pat. No. 6,907.

The primary objective of this breeding was to produce a new rose variety having the compact, well branched growth habit and lovely flowr form of DICmagic combined with the distinctive flower petal markings of the male parent. The objective was substantially achieved, along with other desirable improvements, as evidenced by the following unique combination of characteristics that are outstanding in the new variety and that distinguish it from its parents, as well as from all other varieties of which I am aware:

1. Distinctive yellow and orange, hand-painted like flowers;
2. Dark green, healthy, disease-resistant foliage;
3. Upright, well-branched growth habit; and
4. High-centered flowers borne in large clusters.

Asexual reproduction of this new variety by budding and softwood cuttings, as performed at Wasco, Calif. and Newtownards, County Down, Northern Ireland, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—DICmagic.

*Pollen parent.*—MACmanly.

Classification:

*Botanical.*—*Rosa hybrida.*

*Commercial.*—Floribunda.

FLOWER

Observations made from specimens grown in garden environments in Somis, Calif., and Newtownards, County Down, Northern Ireland.

Blooming habit: Continuous.

Bud:

*Size.*—$\frac{3}{4}$ inches long when the petals start to unfurl.

*Form.*—Short; pointed ovoid.

*Color.*—When sepals first divide, bud color is Yellow-Orange Group 14C. When half blown, the upper sides of the petals are Yellow-Orange Group 14C with Orange Group 28A in the middle section of each petal; and the lower sides of the petals are Yellow Group 14C.

*Sepals.*—Color: Green Group 138B. Surface texture: Covered in fine hairs. There are three lightly appendaged sepals. There are two unappendaged sepals with hairy edges.

*Receptacle.*—Color: Green Group 137C. Shape: Apple. Size: Small ($\frac{1}{4}$ inch$\times\frac{1}{4}$ inch). Surface: Smooth.

*Peduncle.*—Length: Short (1 to $1\frac{1}{2}$ inches). Surface: Glandular. Color: Bronzy. Strength: Stiff, erect.

Bloom:

*Size.*—Medium. Average open size is 3 to $3\frac{1}{2}$ inches in diameter.

*Borne.*—Several together in rounded clusters with 3 to 10 flowers.

*Stems.*—Medium (12 to 18 inches), strong.

*Form.*—When first open: High centered. Permanence: Flattens, all petals curl.

*Petalage.*—Number of petals under normal conditions: 20.

*Color.*—The upper side of the petals is Orange-Yellow Group 14C with hand-painted like Orange Group 28A in the center portion of each petal. The major color on the upper side is Yellow Group 14C. The reverse side of the petals is Orange-Yellow Group 14C with the orange coloration of the upper surface showing through on at least some petals.

*Variegations.*—None.

*Discoloration.*—The genral tonality at the end of the first day: No change. At the end of the third day: Gradual fading to Orange Group 28D.

*Fragrance.*—Slight.

Petals:

*Texture.*—Thick.

*Shape.*—Round to deltoid.

*Form.*—Tips are slightly recurved.

*Arrangement.*—Imbricated, with a few petaloids in the center.

*Persistence.*—Drop off cleanly.

*Lastingness.*—On the plant: Fair (4 to 5 days). As a cut flower: Short (3 to 4 days).

Reproductive parts:

*Anthers.*—Size: Medium. Quantity: Many. Color: Yellow. Arrangement: Regular around the styles.

*Filaments.*—Color: White.

*Pollen.*—Color: Gold-yellow.

*Styles.*—Color: Yellow.

*Stigmas.*—Greenish-white.

Form: Bush.

Growth: Vigorous; upright; branching; plant height or 3 to 3½ feet and plant width of 2 to 2½ feet.

Foliage:

*Number of leaflets on normal mid-stem leaves.*—5 or 7.

*Size.*—Medium (5 inches×3 inches).

*Quantity.*—Normal.

*Color.*—New foliage: Bronze (Greyed-Purple Group 183A). Old Foliage: Green Group 141A.

Leaflets:

*Shape.*—Pointed oval.

*Texture.*—Upper side: Leathery and glossy.

*Edge.*—Serrated.

*Serration.*—Single.

*Petiole rachis.*—Color: Reddish when young, then green.

*Petiole underside.*—Rough, with occasional prickles.

*Stipules.*—Medium and bearded.

*Disease resistance.*—Resistant to mildew and rust under normal growing conditions at Somis, Calif., and Newtownards, County Down, Northern Ireland.

Wood:

*New wood*—Color: Reddish. Bark: Smooth.

*Old wood.*—Color: Green. Bark: Smooth.

Prickles:

*Quantity.*—Ordinary on main canes from base. Ordinary on laterals from main canes.

*Form.*—Medium (¼ inch); straight.

*Color when young.*—Red.

Small prickles:

*Quantity.*—None on main stalks. None on laterals.

I claim:

1. A new and distinct variety of rose plant of the floribunda class, substantially as herein shown and described, characterized particularly as to novelty by its well-formed, attractive flowers borne in large clusters; its distinctive yellow and orange colored flowers; its dark green, healthy, disease-resistant foliage; and its upright, well-branched and vigorous growth habit.

* * * * *

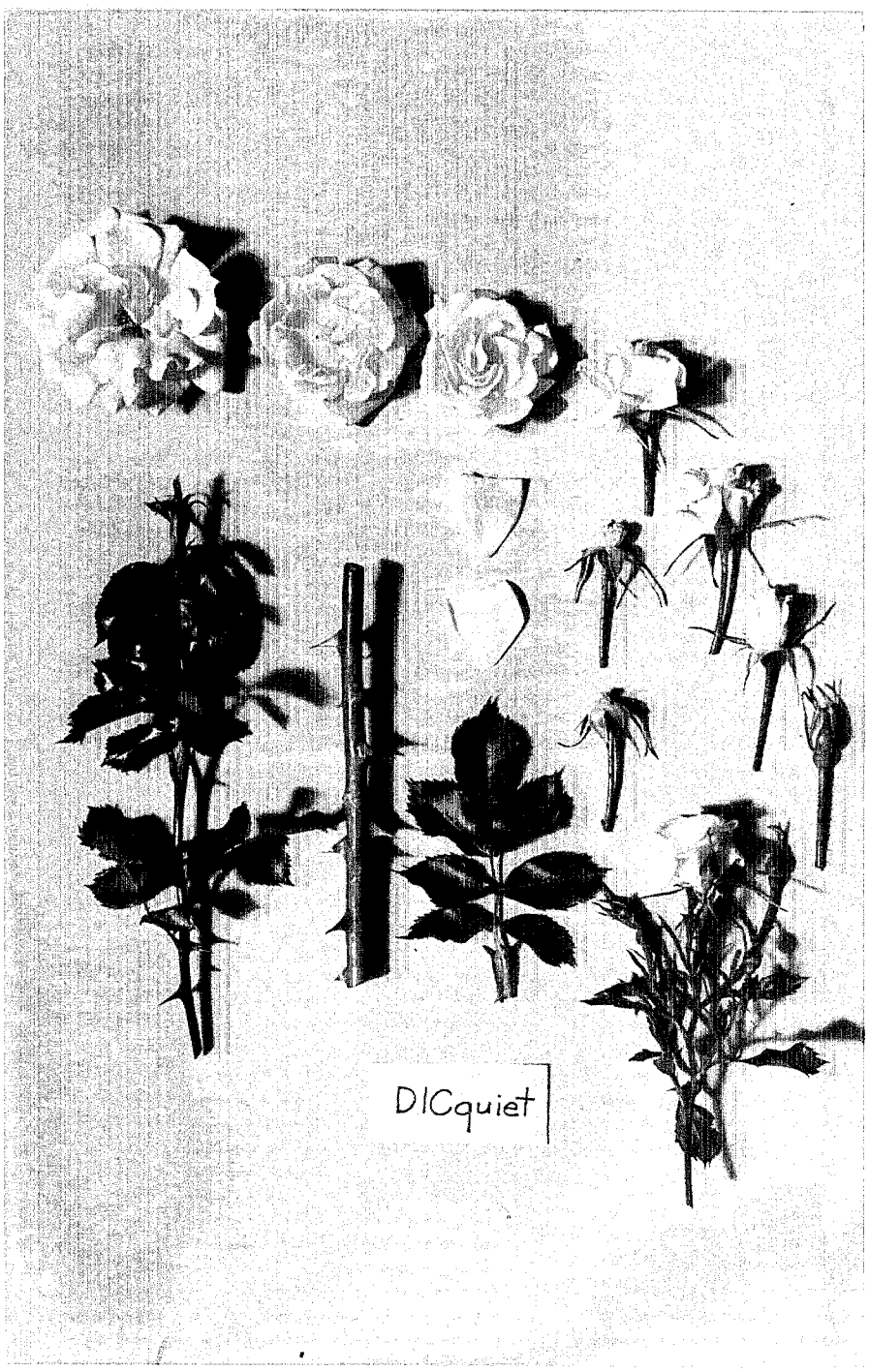
DICquiet

UNITED STATES PATENT AND TRADEMARK OFFICE

CERTIFICATE OF CORRECTION

PATENT NO. : Plant 8,900

DATED : September 20, 1994

INVENTOR(S) : Patrick Dickson

It is certified that error appears in the above-identified patent and that said Letters Patent is hereby corrected as shown below:

Column 1, line 7, "flowr" should read --flower--.

Signed and Sealed this

Twelfth Day of November, 1996

*Attest:*

Bruce Lehman

BRUCE LEHMAN

*Attesting Officer*

*Commissioner of Patents and Trademarks*